United States Patent [19]

Bazzato

[11] 4,306,976
[45] Dec. 22, 1981

[54] METHOD AND DEVICE FOR AMBULATORY PERITONEAL DIALYSIS

[75] Inventor: Giorgio Bazzato, Padua, Italy

[73] Assignee: Bieffe S.p.A., Sondrio, Italy

[21] Appl. No.: 104,294

[22] Filed: Dec. 17, 1979

[30] Foreign Application Priority Data

May 25, 1979 [IT] Italy ................................ 22971 A/79

[51] Int. Cl.³ ........................ A61M 5/00; B01D 13/00
[52] U.S. Cl. ................................. 210/646; 128/213 A
[58] Field of Search ............................ 210/321 A, 22; 128/213 A, 214 R, 221

[56] References Cited

U.S. PATENT DOCUMENTS

| 3,709,222 | 1/1973 | DeVries | 128/213 A |
| 3,902,489 | 9/1975 | Carter | 128/214 R |
| 4,034,754 | 7/1977 | Virag | 128/221 X |

FOREIGN PATENT DOCUMENTS 145313 12/1961 U.S.S.R. .......................... 128/213 A

Primary Examiner—Frank A. Spear, Jr.
Attorney, Agent, or Firm—Holman & Stern

[57] ABSTRACT

A method and apparatus for ambulatory intraperitoneal dialysis, comprising at least two containers one filled with unused dialysis fluid and one empty, each container being provided with flow regulating means and with a connecting tube ending in a Y-shaped junction whose common branch is connected to a third tube, provided at its free end with a sterile needle. The needle is inserted in a second Y-shaped junction having two branches each containing two membranes which form therebetween a sterilizing liquid chamber. The common channel of the second Y-shaped junction is connected to an external portion of an intraperitoneal catheter. By appropriate positioning of the containers and operation of the regulating means, used solution may be drained and fresh solution introduced.

8 Claims, 2 Drawing Figures

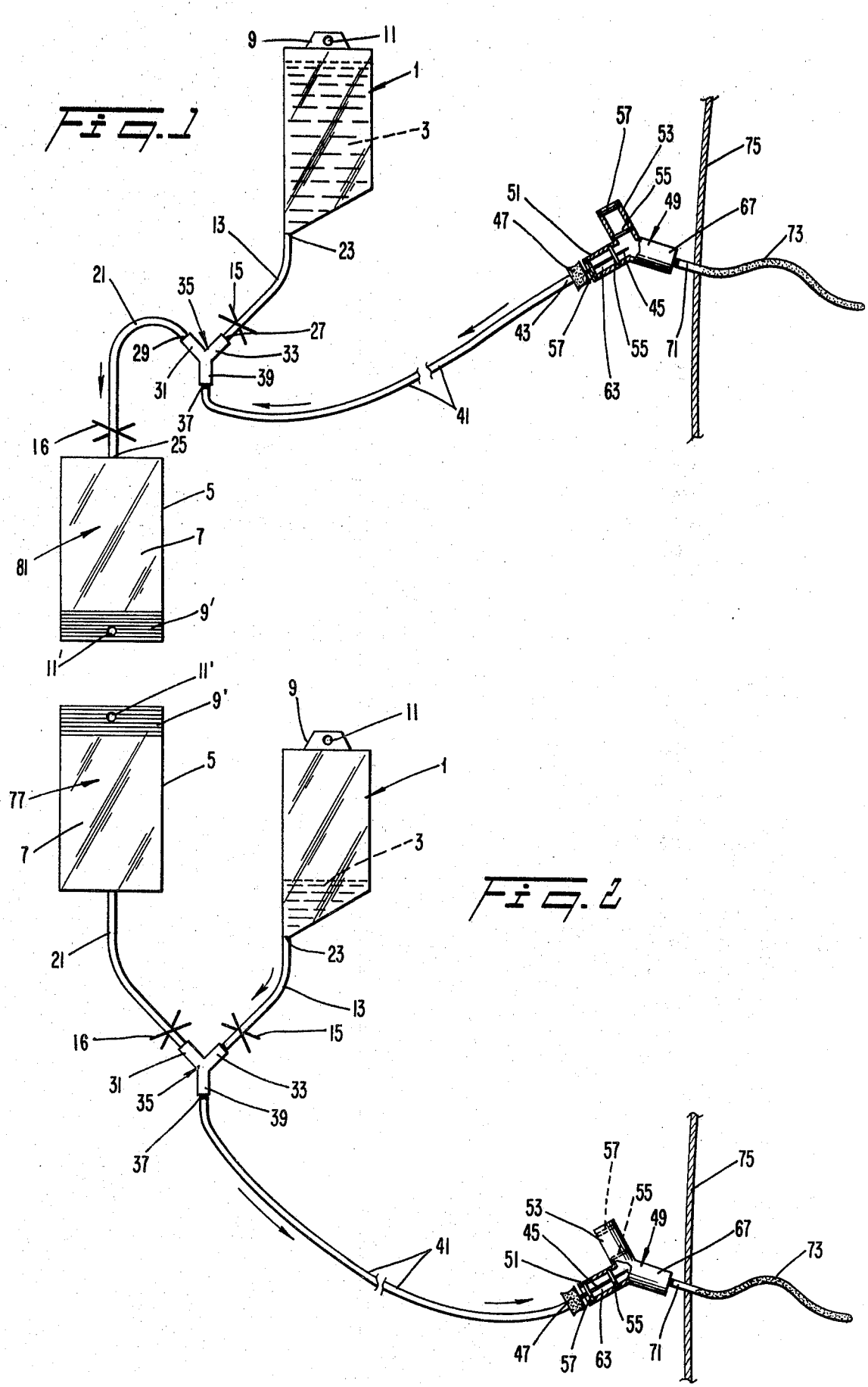

METHOD AND DEVICE FOR AMBULATORY PERITONEAL DIALYSIS

BACKGROUND OF THE INVENTION

1. Field of the Invention

The present invention relates to a method for the ambulatory peritoneal dialysis, in which a dialysis solution is brought through a catheter in the peritoneal cavity, is left there for the time requested to transfer into it the toxic substances and the water contained in the blood, and is then taken out.

More particularly the invention concerns a peritoneal dialysis system in which the exhausted liquid drained from the peritoneal cavity is housed in a container which is separate from the container in which the fresh solution to be fed to said cavity is housed. The invention also comprises the device for the embodiment of the above system.

2. Description of the Prior Art

A method recently developed in Canada and USA is known in which a sterile quantity of solution is transfered from a single flexible atoxic plastic bag to the peritoneal cavity of a patient through a simple connection system to the infusion set using various connecting technics between bag and set and between set and catheter. These connections are made in the "open" and can be the causes of peritonitis complications. As presently employed, the U.S. and Canadian system calls for the collection of the used dialysis solution from the peritoneal cavity in the same bag which contained the fresh solution before its injection into the peritoneal cavity. The bag is rolled up and kept on the patient's body in several ways, e.g. placed in a cloth packet suspended around the waist of the patient till the next dialysis at an interval of about 5 hours. This involves obviously remarkable inconvenience for the patient who is obliged to carry the uncomfortable bag.

The clinic statistics report several incidents of septic peritonitis due just to the repeated connections of the infusion set to the dialysis liquid bag, these connections are carried out outside the hospital (at home, office, factory, etc.) by the patient himself on an "open" junction.

SUMMARY OF THE INVENTION

The first object of the present invention is a device comprising more inter-connected bags, one of which is initally empty and receives the exhausted liquid drained from the peritoneal cavity while the other bag contains the peritoneal dialysis liquid (e.g. two liters) with which the solution just drained from the peritoneal cavity can be immediatly replaced without reconnecting a new dialysis bag. The patient is thus rendered entirely free and independent from the system during the period between exchanges. Another object of the invention is to eliminate the septic peritonitis by use of a particular puncturable connection between the sterile needle associated with the bag system and the puncturable membranes of the Y-shaped junction of the peritoneal catheter. Another object of the invention is to avoid direct communication of the peritoneum with the outside air through an open catheter, by supplying the catheter with a "Y" junction having a closed puncturable membrane. This system reduces the chance of contaminating the peritoneum.

Finally, to further reduce the risk of peritoneal infection, an intermediate chamber has been provided in the "Y" junction of the catheter. This chamber is limited by two puncturable membranes between which is contained a sterilizing liquid which provides a further barrier to the introduction of the bacteria at the moment of the needle insertion.

These and other objects of the invention are obtained with the method of the present invention, characterized in that the tubular ends of each container for feeding the fresh solution and drawing the exhausted solution are provided with means for regulating defluxion of the fluids; the feed of the dialysis solution to the peritoneal cavity is carried out by closing the flow regulating means of the draining container opening the flow regulating means of the feeding container and letting the fresh solution flow through a first junction to a common passage which is connected to protected hollow puncturing means to a junction of the catheter connector; the peritoneal cavity is drained of the exhausted solution by closing the flow regulating means of the fresh solution container, opening the flow regulating means of the exhausted solution container and moving the exhausted solution container to a level below the catheter thereby allowing the fluid to flow through the catheter and first junction means and into the solution collecting container.

The device for the reduction to practice of the above method is characterized in that it comprises, besides the fresh dialysis solution container, a second container to collect the exhausted liquid drained from the peritoneal cavity, both containers being provided with tubular ends showing defluxion or flow controlling means; a first Y-shaped junction for the two tubular ends of said containers; a common tube which starts at said first junction and terminates at the other end with a hollow needle and is thereby inserted in a second y-shaped junction by perforating two membranes which are associated to each input branch of said second junction, are water-tight with the junction branches and are at a short distance from the one another so to form an antiseptic liquid chamber; and a catheter junction inserted in the common branch of said Y-shaped junction.

According to a feature of the invention, the two containers are bags in atoxic flexible plastic material selected from the group consisting of films of vinyl chloride polymers or of one or more mono-olefins, and of laminates comprising a film of polyethylene with a little butylene, a film of polyamide-6 and/or a film of polypropylene with or without a little ethylene.

Advantageously the puncture needle is protected and kept in a sterile condition by a cap of plastic material.

BRIEF DESCRIPTION OF THE DRAWING

The various features and advantages of the invention will better appear from the description of the notlimiting embodiment shown in the attached drawings in which FIGS. 1 and 2 are schematic front views illustrating the above system, FIG. 1 showing the draining phase and FIG. 2 showing the filling phase.

DETAILED DESCRIPTION OF THE PREFERRED EMBODIMENTS

In these embodiments 1 indicates a first bag destined to contain the dialysis solution 3, and 5 denote a second bag destined to receive the liquid coming out of the peritoneal cavity 7. The bag 1 shows at one end an expansion 11 with a hole 9 for its suspension or hanging and, at the opposite end, at least one small tube 13 which can be closed and opened with the aid of a defluxion or flow controlling means 15. Also, as the figures illustrate, the bag 5 shows a rib or expansion 9 provided with a hanging hole 11 and a connecting tube 21; the latter provided with a defluxion or flow control means 16. Both tubes 13 and 21 have their ends 23 and 25 attached to the bags 1 and 5 respectively and the opposite ends 27 and 29 are inserted into branches 31 and 33 of a Y-shaped junction 35 whose common branch 37 is connected to an end 39 of a third tube 41 which tube is provided at the other (free) end 43 with sterile needle 45 protected by a cap 47.

The sterile needle 45 can be inserted in a second Y-shaped junction 49 having two branches 51 and 53. These two branches have a particular structure in the form of two membranes 55 and 57 which are punctured by the sterile needle 45 and each pair of the membranes forms a sterilizing or antiseptic liquid chamber 63 in the branches 51 and 53 of junction 49. Obviously the membranes are perfectly watertight to avoid leaks especially towards the peritoneal cavity. Into the common branch 67 of junction 49 a connector 71 is inserted which at its other end is connected to the peritoneal catheter 73 passing through the peritoneum 75. The operation should be clear from a comparison of FIGS. 1 and 2 which illustrate the two system steps or phases i.e. the draining phase from the peritoneum as in FIG. 1, and a peritoneum filling phase as in FIG. 2.

Draining phase (FIG. 1)

The collecting bag 5 is empty 81 and is placed below the level of catheter 73; the defluxion or flow regulating means 16 closed while the flow regulating means 15 is open. The needle is inserted in 51. In this phase the liquid which is in the peritoneal cavity and has absorbed the blood wastes, flows, following the course indicated by the arrows, from the peritoneum into the bag 5 which is thus filled.

Filling phase (FIG. 2)

The defluxion or flow regulating means 16 is closed and the bag 5 (filled with the liquid drained from the peritoneum, 75) can now be disgarded. The bag 1 (filled with fresh dialysis solution, e.g. two liters thereof, suspended at its normal level, i.e. that of the dialysis stand) has the defluxion or flow regulating means 15 opened whereby the liquid 3 fills up the peritoneal cavity following the course of the arrows. The bags 1 and 5, the tubes 13, 21 and 41, the junctions 35 and 49 and the cap 47 (covering the sterile needle 45) are all made of atoxic plastic, generally transparent, material made of polymers or copolymers of vinyl chloride or of a monoolefin, e.g. ethylene.

The bags 1 and 5 and the tubes are preferably flexible. It is to be noted that especially for the bags it is advantageous to utilize, instead of a sheet or film made of PVC or of polyethylene, a laminate with two or three layers formed of said film, or for example consisting of layers formed of a film of polyethylene with or without combined monomeric units of butylene (below 10%) and a film of polypropylene (homo or co-polymer with ethylene). Particularly advantageous are two-layer laminates consisting of a polyamide-6 film and of a film of polyethylene with butylene ("Sclair" of Dupont of Canada); or three layer laminates comprising a film of polyethylene with a little butylene ("Sclair"), a film of polyamide-6 (e.g. "Filmon BX" of Snia Viscosa S.p.A.) and a film of "Sclair" or of polypropylene ("Moplefan").

The thicknesses of the above films are in the range of 10 to 80 microns.

The following are substantial advantages of the invention (a) absence of discomfort and inconvience while ensuring maximum freedom for the patient, which will increase the use of this dialysis method which is called "CAPD";

(b) the reduction, practically to zero of the risk of septic peritonitis; and the (c) elimination of contamination risk as the peritoneum is no longer in direct communication with the atmosphere.

I claim:

1. An apparatus for ambulatory intraperitoneal dialysis of a patient in need of such treatment comprising at least two container means, said container means being suitable for containing sterile dialysis fluid, at least one of said container means being filled with unused dialysis fluid, and another of said container means being empty; tubing means connected to each of said container means; a first junction means connected to the other end of said tubing means, said first junction means having at least two channels; flow regulating means interposed between each of said container means and said first junction means; a single common tubing means connected to said first junction means, said common tubing means having at its other end and connected thereto a hollow sterile piercing means; a second junction means, having at least two channels; said channels capable of accepting said piercing means; said channels having two membranes, said membranes being sealably piercable by said piercing means; said two membranes forming a sealed chamber in each of said channels; said chamber having a longitudinal dimension less than the longitudinal dimension of said piercing means; said chamber therein containing a sterilizing or antiseptic medium, said second junction means having a common channel connected to an external portion of a substantially intraperitoneal catheter.

2. The apparatus of claim 1 wherein said container means are bags and said bags are made of atoxic flexible plastic material.

3. The apparatus of claim 2 wherein said flexible plastic material is selected from a group consisting of films of vinyl chloride polymers, films of olefinic homopolymers, films of olefinic copolymers, and of laminates comprising: a film of polyethylene with a small amount of butylene, a film of polyamide-6 and a film of polypropylene with a small amount of ethylene; a film of polyethylene with a small amount of butylene, a film of polyamide-6 and a film of polypropylene without ethylene; a film of polyethylene with a small amount of butylene and a film of polypropylene with a small amount of ethylene; and a film of polyethylene with a small amount of butylene and polypropylene without ethylene.

4. The apparatus of claim 1 wherein said first and second junction means are "Y" shaped tubes.

5. The apparatus of claim 1 wherein said common tubing means connected to said first junction means has at its end means for lockably accepting said hollow piercing means.

6. The apparatus of claim 1 wherein the hollow piercing means is a sterile needle, said needle being protected before use by a plastic material cap.

7. A method of intraperitoneal dialysis of a patient in need of such treatment comprising the steps of:
I. providing at least two container means one filled with fresh dialysis solution and one empty,
  (a) interconnecting each container means through separate tubing means to a first junction means,
  (b) interposing fluid flow controlling means between each of said container means and said first junction means,
  (c) providing said first junction means with a common tubing means connected thereto,
  (d) providing said common tubing means on its free end with a sterile hollow puncturing means,
  (e) connecting said common tubing means to a closed intraperitoneal catheter by puncturing a pair of sealably puncturable membranes located in the channels of a second junction means, said membranes having between them a reservoir of sterilizing or antiseptic solution;
II. emptying the peritoneum of said patient of used dialysis solution by
  (a) closing the fluid flow controlling means interposed between said container filled with fresh dialysis solution and said first junction means,
  (b) opening the fluid flow controlling means interposed between said empty container means and said first junction means,
  (c) lowering said empty container means below the level of said intraperitoneal catheter and filling said empty container means with said used dialysis solution;
III. and filling the peritoneum of said patient by,
  (a) closing said fluid flow controlling means interposed between the container now filled with used dialysis solution,
  (b) opening said fluid flow controlling means interposed between the container filled with fresh dialysis solution,
  (c) raising said container filled with fresh dialysis solution above the level of the intraperitoneal catheter and filling the peritoneum of said patient with fresh dialysis solution.

8. The method of claim 7 wherein at the conclusion of filling the peritoneum of said patient, disconnecting said common tubing means from said intraperitoneal catheter and permitting the patient to move about unencumbered by the dialysis apparatus used during the period of intraperitoneal dialysis.

* * * * *